United States Patent [19]

Wirth et al.

[11] Patent Number: 4,931,576
[45] Date of Patent: Jun. 5, 1990

[54] PROCESS FOR PRODUCING GLYCIDYL THIOETHERS

[75] Inventors: Hermann O. Wirth, Bensheim; Hans-Helmut Friedrich, Lautertal, both of Fed. Rep. of Germany

[73] Assignee: Ciba-Geigy Corporation, Ardsley, N.Y.

[21] Appl. No.: 213,509

[22] Filed: Jun. 28, 1988

Related U.S. Application Data

[63] Continuation of Ser. No. 18,793, Feb. 20, 1987, abandoned, which is a continuation of Ser. No. 750,618, Jul. 1, 1985, abandoned.

[30] Foreign Application Priority Data

Jun. 29, 1984 [CH] Switzerland ............... 3148/84

[51] Int. Cl.$^5$ ........................................... C07D 303/34
[52] U.S. Cl. ................................. 549/514; 549/556
[58] Field of Search .................... 549/514, 556

[56] References Cited

U.S. PATENT DOCUMENTS

| | | | |
|---|---|---|---|
| 2,434,099 | 1/1948 | Bousquet | 549/556 |
| 2,731,437 | 1/1956 | Bender et al. | 549/514 |
| 2,965,652 | 12/1960 | Gaertner . | |
| 4,284,573 | 8/1981 | Arnett et al. | 549/517 |
| 4,284,574 | 8/1981 | Bagga | 549/555 |
| 4,373,073 | 2/1983 | Wojtech et al. | 549/517 |
| 4,540,802 | 9/1985 | Tomita et al. | 549/517 |

FOREIGN PATENT DOCUMENTS

| | | |
|---|---|---|
| 909793 | 9/1972 | Canada . |
| 0028810 | 5/1981 | European Pat. Off. . |
| 121260 | 10/1984 | European Pat. Off. . |
| 1352527 | 5/1974 | United Kingdom . |
| 1359289 | 7/1974 | United Kingdom . |

OTHER PUBLICATIONS

J. M. McIntosh, Journal of Chemical Education, vol. 55(4), Apr. 1978, pp. 235–238.
G. W. Gokel et al., Journal of Chemical Education, vol. 55(6), Jun. 1978, pp. 350–354.
W. P. Weber et al., Journal of Chemical Education, vol. 55(7), Jul. 1978, pp. 429–433.
C. Starks, Chemtech, Feb. 1980, pp. 110–117.
CA, 50, 7503d (1956).
Chem. Abst. 57, 6267c.
Karel Verschuren, Handbook of Environmental Data on Organic Chemicals, Van Nostrand Reinhold Co., 2nd ed., pp. 611–613.
Marshall Sittig, Hazardous and Toxic Effects of Industrial Chemicals, Noyes Data Corp., (1979), pp. 192–194.
Marshall Sittig, Handbook of Toxic Hazardous Chemicals and Carcinogens, Noyes Publications, 2nd ed., pp. 399–401.
Registry of Toxic Effects of Chemical Substances, 1981–1982 Edition, vol. 3, U.S. (HHS), 1983, pp. 287–288.
N. Irving Sax, Dangerous Properties of Industrial Materials, Van Nostrand Reinhold & Co., 6th edition, pp. 709 to 710.

Primary Examiner—Glennon H. Hollrah
Assistant Examiner—Amelia A. Owens
Attorney, Agent, or Firm—JoAnn Villamizar

[57] ABSTRACT

A process for producing glycidylthio ethers of the formula I

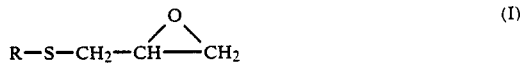

which process comprises reacting epichlorohydrin with a mercaptan of the formula II

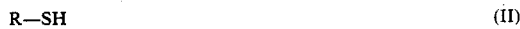

in which R can be a radical

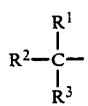

wherein $R^1$, $R^2$ and $R^3$ independently of one another are each $C_1$–$C_{18}$-alkyl, and together contain no more than 22 C atoms, and $R^2$ and $R^3$ are in addition hydrogen, or wherein R is $C_5$–$C_6$-cycloalkyl, phenyl or naphthyl unsubstituted or substituted by $C_1$–$C_4$-alkyl, or is benzyl or furfuryl, or wherein R is $C_2$–$C_8$-alkylene which is substituted by —SH and which can be interrupted by 1 or 2 ether-O atoms, in an equimolar amount, without organic solvent and in the presence of a base, the reaction being performed by the phase-transfer catalysis process, wherein a phase-transfer catalyst is used, at a temperature of $-30°$ C. to $+20°$ C. The glycidyl thioethers thus obtained are compounds that play an important part in the synthesis of organic sulfur compounds, which are used for example as lubricant additives.

7 Claims, No Drawings

PROCESS FOR PRODUCING GLYCIDYL THIOETHERS

This application is a continuation of application Ser. No. 018,793, filed 2/20/87, abandoned, which is a continuation of application Ser. No. 750,618, filed on 7/1/85, now abandoned.

The present invention relates to a process for producing glycidyl thioethers.

Glycidyl thioethers are compounds that play an important part in the synthesis of organic sulfur compounds, which are used for example as lubricant additives.

The production of glycidyl thioethers is known per se, and is described in U.S. PAT. Nos. 2,965,652 and 2,731,437, as well as in the Canadian Patent Specification No. 909,793. These processes use epichlorohydrin in excess and also organic solvents, factors which are undesirable for reasons of industrial hygiene and safety. Furthermore, a process which does not involve the use of an excess of epichlorohydrin, but which gives an unsatisfactory yield of glycidyl thioethers is known from the G.B. Patent Specification No. 1,352,527.

There has now been found a process which does not have these risk factors, and which moreover gives high yields of glycidyl thioethers.

Subject matter of the present invention is a process for producing glycidyl thioethers of the formula I

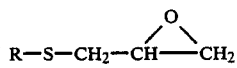
(I)

which process comprises reacting epichlorohydrin with a mercaptan of the formula II

R—SH (II)

in which R can be a radical

wherein $R^1$, $R^2$ and $R^3$ independently of one another are each $C_1$–$C_{18}$-alkyl, and together contain no more than 22 C atoms, and $R^2$ and $R^3$ are in addition hydrogen, or wherein R is $C_5$–$C_6$-cycloalkyl, phenyl or naphthyl unsubstituted or substituted by $C_1$–$C_4$-alkyl, or is benzyl or furfuryl, or wherein R is $C_2$–$C_8$-alkylene which is substituted by —SH and which can be interrupted by 1 or 2 ether-O atoms, in an equimolar amount, without organic solvent and in the presence of a base, the reaction being performed by the phase-transfer catalysis process, wherein a phase-transfer catalyst is used, at a temperature of $-30°$ C. to $+20°$ C.

When R is a radical of the form

it can be $R^1$—$CH_2$—,

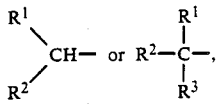

wherein $R^1$, $R^2$ and $R^3$ are each $C_1$–$C_{18}$-alkyl. For $C_1$–$C_{18}$-alkyl, the substituents are straight-chain or branched-chain, for example: methyl, ethyl, n-propyl, isopropyl, n-butyl, isobutyl, sec-butyl, tert-butyl, straight-chain or branched-chain pentyl, hexyl, heptyl, octyl, nonyl, decyl, undecyl, dodecyl, tridecyl, tetradecyl, pentadecyl, hexadecyl, heptadecyl or octadecyl. The preferred radical is

wherein $R^1$, $R^2$ and $R^3$ together with the C atom to which they are bound form $C_4$–$C_{20}$-alkyl, and none of the substituents $R^1$, $R^2$ and $R^3$ may be hydrogen. Particularly preferred is $C_4$–$C_{16}$-alkyl, and especially preferred is tert-butyl, tert-nonyl (ex Phillips Petroleum) or tert-dodecyl, by tert-dodecyl being meant for example a radical such as is described for tertiary dodecylmercaptan in "Ullmanns Enzyklopädie der technischen Chemie, 4th Edition, Vol. 23, pp. 181–182, Verlag Chemie, Weinheim".

When R is $C_5$–$C_6$-cycloalkyl, it is cyclopentyl or cyclohexyl, preferably cyclohexyl.

If R is phenyl or naphthyl substituted by $C_1$–$C_4$-alkyl, the phenyl or naphthyl can be mono- to trisubstituted, preferably however monosubstituted; $C_1$–$C_4$-alkyl is: methyl, ethyl, n-propyl, isopropyl, n-butyl, isobutyl, sec-butyl or tert-butyl.

When R is SH-substituted $C_2$–$C_8$-alkylene, which can be interrupted by 1 or 2 ether-O atoms, it is monosubstituted $C_2$–$C_8$-alkylene, the substitution by the —SH group being possible in any position, preferably however in the terminal position; R is in particular —$CH_2$—$CH_2$—SH.

Preferred glycidyl thioethers of the formula I obtained by the process according to the invention are those formed from epichlorohydrin and a mercaptan of the formula II wherein R is a radical of the form

wherein $R^1$, $R^2$ and $R^3$ independently of one another are each $C_1$–$C_{18}$-alkyl, and together contain no more than 22 C atoms, and $R^2$ and $R^3$ are in addition hydrogen, or wherein R is $C_2$–$C_8$-alkylene which is substituted in the terminal position by the —SH group, and which can be interrupted by 1 or 2 ether-O atoms.

Particularly preferred glycidyl thioethers of the formula I are produced in the process according to the invention by reaction of epichlorohydrin with a mercaptan of the formula II, in which R is a radical of the form

CHEMTECH, February, 1980, p. 111, Table 1, for example quaternary salts, polyethers and N-alkylphosphoramides.

TABLE 1

| Types of anion transfer catalysts | |
|---|---|
| | Typical structures |
| Quaternary salts | $R_4N^+X^-, R_4P^+X^-, R_4As^+X^-$, usually R = alkyl, benzyl |
| Cyclic polyethers | 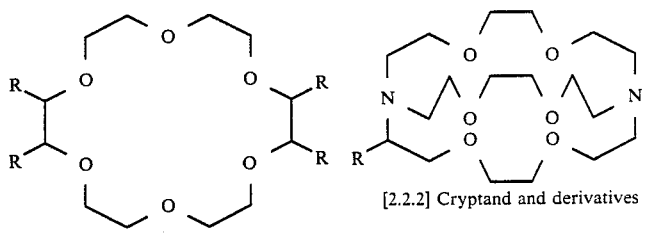 18-Crown-6-and derivatives     [2.2.2] Cryptand and derivatives |
| Open-chain polyethers | $R(\text{—OCH}_2\text{CH}_2)_n\text{OR}'$   $n \geq 8$     Ethoxylates, R = alkyl, sometimes H |
| | 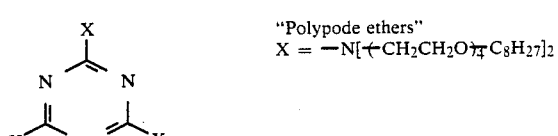 "Polypode ethers" $X = -\text{N}[(\text{—CH}_2\text{CH}_2\text{O})_4\text{C}_8\text{H}_{27}]_2$ |
| | 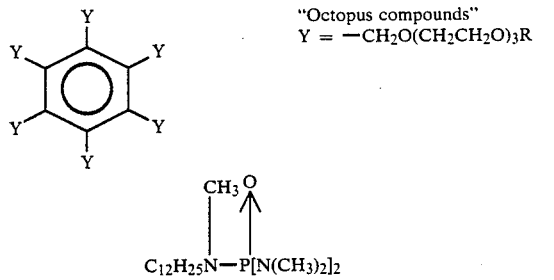 "Octopus compounds" $Y = -\text{CH}_2\text{O}(\text{CH}_2\text{CH}_2\text{O})_3\text{R}$ |
| N-Alkylphosphoramides | 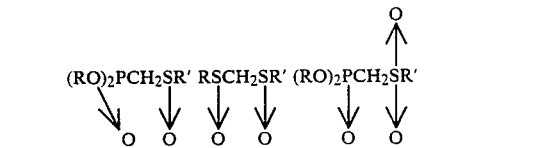 |
| Methylene-bridged phosphorous and sulfur oxides |  |

$$R^2-\underset{R^3}{\overset{R^1}{\underset{|}{\overset{|}{C}}}}-,$$

wherein $R^1$, $R^2$ and $R^3$ together with the C atom to which they are bound form $C_4$-$C_{20}$-alkyl, and none of the substituents $R^1$, $R^2$ and $R^3$ may be hydrogen, or wherein R is —CH$_2$CH$_2$—SH.

The process according to the invention is performed in the presence of a base which, relative to the reactant mercaptan, is used in an equimolar amount or in a slight excess. Suitable bases are for example: alkali metal hydroxides, such as sodium, potassium or lithium hydroxide, or alkaline-earth metal hydroxides, such as calcium or magnesium hydroxide. The base preferably used is an alkali metal hydroxide, particularly sodium hydroxide.

The process according to the invention is performed in the presence of a phase-transfer catalyst, which is used in a customary amount, for example at least 0.6% by weight, relative to the employed amount of mercaptan and epichlorohydrin. Various phase-transfer catalysts are suitable, such as are listed for example in There are preferably used in the process according to the invention quarternary ammonium salts of the formula III $$R^b-\underset{R^c}{\overset{R^a}{\underset{|}{\overset{|}{N^\oplus}}}}-R^d \quad X^\ominus \tag{III}$$

wherein $R^a$, $R^b$, $R^c$ and $R^d$ are identical or different, and are straight-chain or branched-chain alkyl groups, all four alkyl groups together containing 4 to 20 C atoms, or are benzyl, and $X^\ominus$ is —Br$^\ominus$, —Cl$^\ominus$, HSO$_4{}^\ominus$ or CH$_3$SO$_4{}^\ominus$.

$R^a$, $R^b$, $R^c$ and $R^d$ can be the following alkyl groups, for example: methyl, iso-propyl, n-butyl, sec-butyl, tert-butyl, tert-amyl, 2-ethylhexyl, n-octyl, 1,1,3,3-tetramethylbutyl and n-dodecyl.

The phase-transfer catalyst preferably used is (n—C$_4$H$_9$)$_4$NCl and (n—C$_4$H$_9$)$_4$NBr, especially (n—C$_4$H$_9$)$_4$NBr.

The reaction of the reactants in the process according to the invention is performed at a temperature of $-30°$ C. to $+20°$ C., preferably at a temperature of $10°-20°$ C., and the maximum temperature is not to be exceeded.

Phase separation for viscous reaction products is effected preferably at elevated temperature.

In a preferred embodiment of the process according to the invention, the mercaptan of the formula II, the epichlorohydrin and the phase-transfer catalyst are placed into the reaction vessel and, at a temperature of below 20° C., a catalytic amount of an aqueous solution of the base is added and subsequently the remainder of the base in aqueous solution.

A particularly preferred embodiment of the process according to the invention comprises placing the mercaptan of the formula II and the phase-transfer catalyst into the reaction vessel and then adding, at a temperature of below 20° C., the epichlorohydrin and a catalytic amount of an aqueous solution of the base and subsequently the remainder of the base in aqueous solution.

The epichlorohydrin and the catalytic amount of base are preferably added separately but simultaneously.

The catalytic amount of the base is approximately 2 to 5% of the total amount of base.

It is possible to automate the process according to the invention, for example the addition of epichlorohydrin by temperature measurement, and the addition of the base by pH measurement.

The following are examples of the glycidylthio ethers of the formula I obtainable by the process according to the invention:
tert-octylglycidyl thioether,
n-octylglycidyl thioether,
tert-nonylglycidyl thioether,
tert-dodecylglycidyl thioether,
n-dodecylglycidyl thioether,
tert-hexadecylglycidyl thioether,
cyclohexylglycidyl thioether,
α-naphthylglycidyl thioether,
benzylglycidyl thioether,
furfurylglycidyl thioether, and
ethylene-diglycidyl thioether.

EXAMPLE 1: tert-Octylglycidyl thioether

A solution of 66 parts by weight of sodium hydroxide, 300 parts by weight of water and 8 parts by weight of tetrabutylammonium chloride is added dropwise within 70 minutes at 15° to 20° C., with stirring and partial cooling (particularly at the commencement of the addition) to a mixture of 219 parts by weight of tert-octylmercaptan and 135 parts by weight of epichlorohydrin. The reaction mixture is subsequently stirred at 50° C. for 1 hour; the aqueous phase is then separated, and the organic phase is washed with 200 parts by weight of water. The organic phase is finally distilled in vacuo to thus obtain the tert-octylglycidyl thioether as a colourless liquid having a boiling point of 74° to 75° C. at 0.02 mbar, and a refractive index of $n_D^{20} = 1.4803$; the yield is 250 parts by weight, which corresponds to 82% of the theoretical yield.

EXAMPLE 2: tert-Nonylglycidyl thioether 321 g of tert-nonylmercaptan, 184 g of epichlorohydrin and 4 g of tertrabutylammonium chloride are placed into a 1 liter Sovirel reactor (double-walled reaction vessel) provided with thermometer, stirrer, dosing dropping-funnel and reflux condenser. To this solution are added dropwise within 45 minutes, with stirring and intensive water cooling, 30 ml of a 22% aqueous sodium hydroxide solution and, after subsidence of the exothermic reaction, a further 285 ml of the 22% sodium hydroxide solution are added dropwise at 15°-20° C. within 60 minutes. The reaction mixture is subsequently stirred at 50° C. for 30 minutes; the aqueous phase is then separated, the organic phase is washed twice with 200 g of water each time, and the organic phase is finally dried in vacuo; residue: 422 g (calculated 433 g); $n_D^{20}$: 1.4813; and the residue, according to NMR, contains 92% by weight of tert-nonylglycidyl thioether.

EXAMPLE 3: n-Octylglycidyl thioether 293 g of n-octylmercaptan and 5 g of tetrabutylammonium chloride are placed into a 1 liter Sovirel reactor (double-walled reaction vessel) fitted with thermometer, stirrer, dropping funnel, dosing dropping-funnel and pH-electrode. To this solution are added dropwise within 80 minutes at a pH value of 11.6–12.0, with stirring and intensive cooling, 184 g of epichlorohydrin. The pH value is maintained constant over the total period of 80 minutes by the corresponding controlled addition of about 10 ml of a 22% aqueous sodium hydroxide solution. The reaction temperature should not exceed 20° C. After completion of the exothermic reaction, 305 ml of 22% sodium hydroxide solution are introduced dropwise within 15 minutes. The reaction mixtue is subsequently stirred at 50° C. for 30 minutes; the aqueous phase is then separated, the organic phase is washed twice with 200 g of water each time, and the organic phase is fractionated in vacuo. The yield is 382 g (94% of theory) with a boiling point of 92°-94° C. at 0.04 mbar and a refractive index of $n_D^{20}$: 1.4718.

The following glycidyl thioethers are produced by a process analogous to the processes described in Examples 2 and 3.

| Formula | Analyt. data ($n_D^{20}$; m.p.) | Produced according to general Example No. | Observations Yield |
|---|---|---|---|
| tert.-C$_{12}$H$_{25}$—S—CH$_2$—CH(—O—)CH$_2$ | 98–110°/0.05 $n_D^{20}$: 1.4790 | 2 | 86% by wt.[2] |
| tert.-C$_{12}$H$_{25}$—S—CH$_2$—CH(—O—)CH$_2$ | | 3 | 90% by wt.[1] |

-continued

| Formula | Analyt. data ($n_D^{20}$; m.p.) | Produced according to general Example No. | Observations Yield |
|---|---|---|---|
| tert.-$C_{12}H_{25}$—S—$CH_2$—CH(—O—)$CH_2$ | 125–28°/0.06 $n_D^{20}$: 1.4717 | 3 | 99% by wt.[1] |
| tert.-$C_{16}H_{33}$—S—$CH_2$—CH(—O—)$CH_2$ | 118–20°/0.06 $n_D^{20}$: 1.4844 | 2 | 93% by wt.[1] |
| —S—$CH_2$—CH(—O—)$CH_2$ | 114–16°/0.8 $n_D^{20}$: 1.5074 | 3 | 95% by wt.[1] |
| $CH_2$(—O—)CH—$CH_2$—S—$CH_2$—$CH_2$—S—$CH_2$—CH(—O—)$CH_2$ | $n_D^{20}$: 1.5473 | 3 | 94% by wt.[3] |

[1] determination of the epoxide content in the crude product by NMR;
[2] after distillation;
[3] determination of the epoxide content in the crude product by potentiometric titration.

What is claimed is:

1. A process for producing a glycidyl thioether of formula I $$R-S-CH_2-CH(-O-)CH_2 \quad (I)$$

which process comprises reacting epichlorohydrin with a mercaptan of the formula II $$R-SH \quad (II)$$

in which R can be a radical $$R^2-\underset{R^3}{\overset{R^1}{C}}-$$

wherein $R^1$, $R^2$ and $R^3$ independently of one another are each $C_1$–$C_{18}$-alkyl, and together contain no more than 22 C atoms, and $R^2$ and $R^3$ are in addition hydrogen, or wherein R is $C_5$–$C_6$-cycloalkyl, phenyl or naphthyl unsubstituted or substituted by $C_1$–$C_4$-alkyl, or is benzyl or furfuryl, or wherein R is $C_2$–$C_8$-alkylene which is substituted by —SH and which can be interrupted by 1 or 2 ether-0 atoms, in an equimolar amount, without organic solvent and in the presence of a base, said base being an alkali metal hydroxide or alkaline earth metal hydroxide, said base being used in an equimolar amount or in slight excess amount relative to the mercaptan, the reaction being performed in the presence of a phase-transfer catalyst wherein the phase-transfer catalyst is a quaternary salt, a polyether or an N-alkylphosphoramide, at a reaction temperature of −30° C. to +20° C.

2. A process according to claim 1, wherein there are produced glycidylthio ethers of the formula I from epichlorohydrin and a mercaptan of the formula II in which R is a radical of the form $$R^2-\underset{R^3}{\overset{R^1}{C}}-,$$

wherein $R^1$, $R^2$ and $R^3$ independently of one another are each $C_1$–$C_{18}$-alkyl, and together contain no more than 22 C atoms, and $R^2$ and $R^3$ are in addition hydrogen, or wherein R is $C_2$–$C_8$-alkylene which is substituted in the terminal position by the —SH group, and which can be interrupted by 1 or 2 ether-0 atoms.

3. A process according to claim 1 wherein there are produced glycidylthio ethers of the formula I by reaction of epichlorohydrin with a mercaptan of the formula II, in which R is a radical of the form $$R^2-\underset{R^3}{\overset{R^1}{C}}-,$$

wherein $R^1$, $R^2$ and $R^3$ together with the C atom to which they are bound form $C_4$–$C_{20}$-alkyl, and none of the substituents $R^1$, $R^2$ and $R^3$ may be hydrogen, or wherein R is —$CH_2CH_2$—SH.

4. A process according to claim 1, wherein the phase-transfer catalyst is a quaternary ammonium salt of the formula III $$R^b-\underset{R^c}{\overset{R^a}{N^\oplus}}-R^d \quad X^\ominus \quad (III)$$

wherein $R^a$, $R^b$, $R^c$ and $R^d$ are identical or different, and are straight-chain or branched-chain alkyl groups, all four alkyl groups together containing 4 to 20 C atoms, or are benzyl, and $X^\ominus$ is —$Br^\ominus$, —$Cl^\ominus$, $HSO_4^\ominus$ or $CH_3SO_4^\ominus$.

5. A process according to claim 1, wherein the phase-transfer catalyst is used in an amount of at least 0.6% by weight, relative to the employed amount of mercaptan and epichlorohydrin.

6. A process according to claim 1, wherein the mercaptan of the formula II, the epichlorohydrin and the phase-transfer catalyst are placed into the reaction vessel and, at a temperature of less than 20° C., a catalytic amount of an aqueous solution of the base is added and subsequently the remainder of the base in aqueous solution.

7. A process according to claim 1, wherein the mercaptan of the formula II and the phase-transfer catalyst are placed into the reaction vessel and, at a temperature of less than 20° C., the epichlorohydrin and a catalytic amount of an aqueous solution of the base are added and subsequently the remainder of the base in aqueous solution.

\* \* \* \* \*